United States Patent [19]
Müller et al.

[11] Patent Number: 5,123,902
[45] Date of Patent: Jun. 23, 1992

[54] METHOD AND APPARATUS FOR PERFORMING SURGERY ON TISSUE WHEREIN A LASER BEAM IS APPLIED TO THE TISSUE

[75] Inventors: Gerhard Müller; Norbert Müller-Stolzenburg, both of Berlin, Fed. Rep. of Germany

[73] Assignee: Carl-Zeiss-Stiftung, Heidenheim, Fed. Rep. of Germany

[21] Appl. No.: 406,527

[22] Filed: Sep. 13, 1989

[30] Foreign Application Priority Data

Sep. 13, 1988 [DE] Fed. Rep. of Germany ....... 3831141

[51] Int. Cl.$^5$ .............................................. A61N 5/00
[52] U.S. Cl. ........................................ 604/21; 604/20; 604/27; 604/28; 604/31; 604/35; 604/43; 604/44; 604/65; 606/4; 606/5; 606/6; 606/15; 606/12; 606/17; 128/395; 128/398
[58] Field of Search ....................................... 606/2-7, 606/10-19; 128/345, 397, 398; 604/20-22, 27, 28, 35, 43, 44, 48, 49, 51-53, 31, 67, 65

[56] References Cited

U.S. PATENT DOCUMENTS

| | | | |
|---|---|---|---|
| 3,769,963 | 11/1976 | Goldman et al. | 606/3 |
| 3,900,034 | 8/1975 | Katz et al. | |
| 4,336,806 | 6/1982 | Clark | 606/15 |
| 4,428,748 | 1/1984 | Peyman et al. | |
| 4,461,294 | 7/1984 | Baron | 606/5 |
| 4,556,057 | 12/1985 | Hiruma et al. | 128/395 |
| 4,686,979 | 8/1987 | Gruen et al. | |
| 4,744,360 | 5/1988 | Bath | |
| 4,799,479 | 1/1989 | Spears | 606/7 |

FOREIGN PATENT DOCUMENTS

| | | | |
|---|---|---|---|
| 246127 | 11/1987 | European Pat. Off. | 606/7 |
| 0266038 | 5/1988 | European Pat. Off. | |
| 8701273 | 3/1987 | World Int. Prop. O. | |
| 8807841 | 10/1988 | World Int. Prop. O. | |

OTHER PUBLICATIONS

"Selective Absorption of Ultraviolet Laser Energy by Human Atheroscleratis Plaque Treated with Tetracycline" by Murphy Chutonan et al; Am. J. Cardiol., vol. 55, May 1, 1985, pp. 1293-1297.
"Excimer Laser Angioplasty: Tissue Ablation, Arteria Response, and Fiber Optic Delivery", D. Singleton et al, IEEE Journal of Quantum Electronics, vol. QE-23, No. 10, Oct. 1987.
"Ophthalmic Lasers", F. L'Esperance, pp. 340-345, The C. V. Mosby Co. 1983.
"Response of the Corneal Epithelium to KrF Excimer Laser Pulses", by J. Taboada et al, Health Physics, vol. 40, pp. 677-683, 1981.
"Excimer Laser Surgery of the Cornea", by S. Trokel et al, American Journal of Ophthalmology, vol. 96, pp. 710-715, 1983.
"Quantitation of Corneal Ablation by Ultraviolet Laser Light", by R. Krueger et al, Archives of Ophthalmology, vol. 103, pp. 1741-1742, 1985.
"Excimer Laser Ablation of the Cornea and Lens", by C. Puliafito et al, Ophthalmology, vol. 92, pp. 741-748, 1985.
"Excimer Laser Photoablation in Glaucoma Filtering Surgery", by M. Berlin et al, American Journal of Ophthalmology, vol. 103, pp. 713-714 1987.
"An Ultrastructural Study of Corneal Incisions Induced by an Excimer Laser at 193nm", by J. Marshall et al, Ophthalmology, vol. 92, pp. 749-757, 1985.
"Endoexcimer Laser Intraocular Ablative Photodecomposition", by M. Pellin et al, American Journal of Ophthalmology, vol. 99, pp. 483-484, 1985.
"Excimer Laser Ablation of the Lens", by T. Nanevicz et al, Archives of Opthalmology, vol. 104, pp. 1825-1829.

Primary Examiner—David M. Shay
Attorney, Agent, or Firm—Walter Ottesen

[57] ABSTRACT

Surgical procedures on biological tissue are carried out with the aid of a laser with substances being applied to the tissue before or during the treatment and these substances are absorbent in the range of the wavelength of the laser beam. A surgical manipulator can be provided and equipped with suction and irrigation channels and the substances can be directed to one of these channels via a metering unit. The application of substances such as sulfisomidine or sulfacetamide increases the ablation rate and reduces the threshold of the ablation process. At the same time, sensitive structures are protected from the damaging effects of the laser radiation as well as from the stray radiation and fluorescence radiation triggered by the laser radiation during the application of microsurgery to the eye.

21 Claims, 11 Drawing Sheets

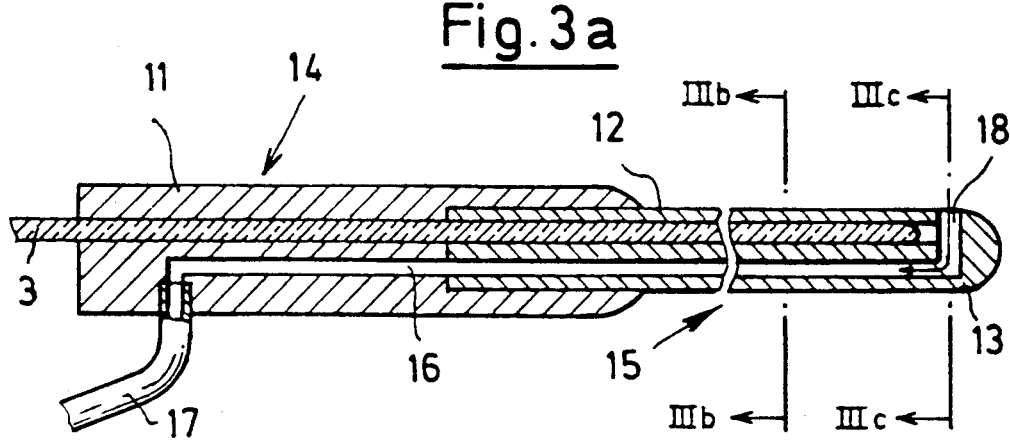
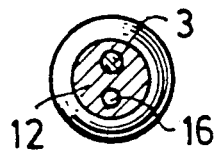
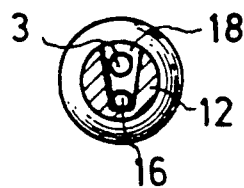
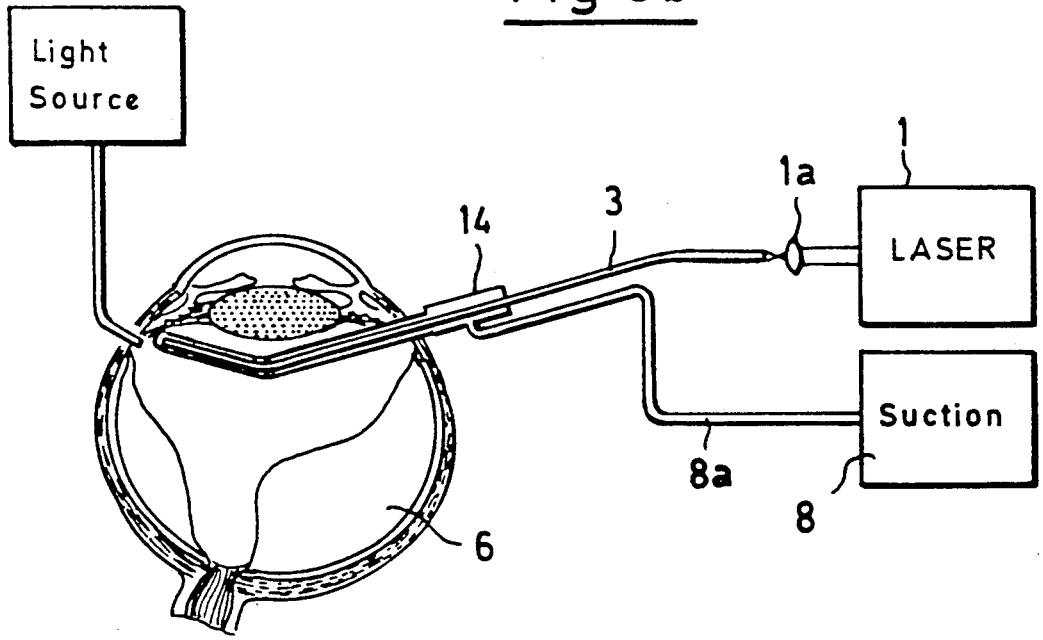

Fig. 4
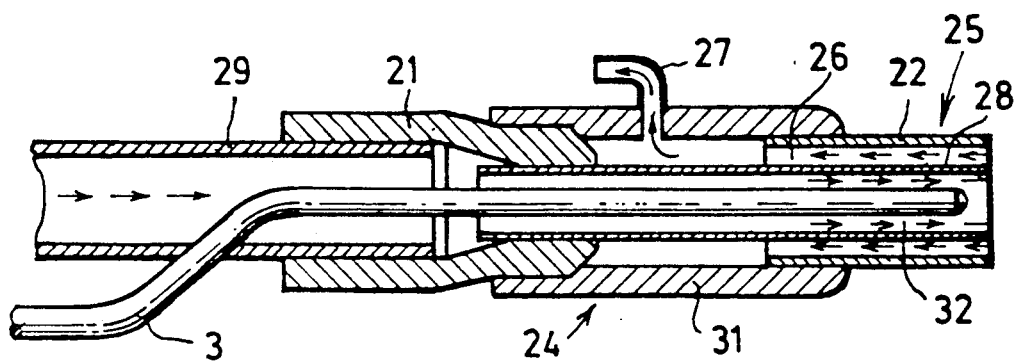
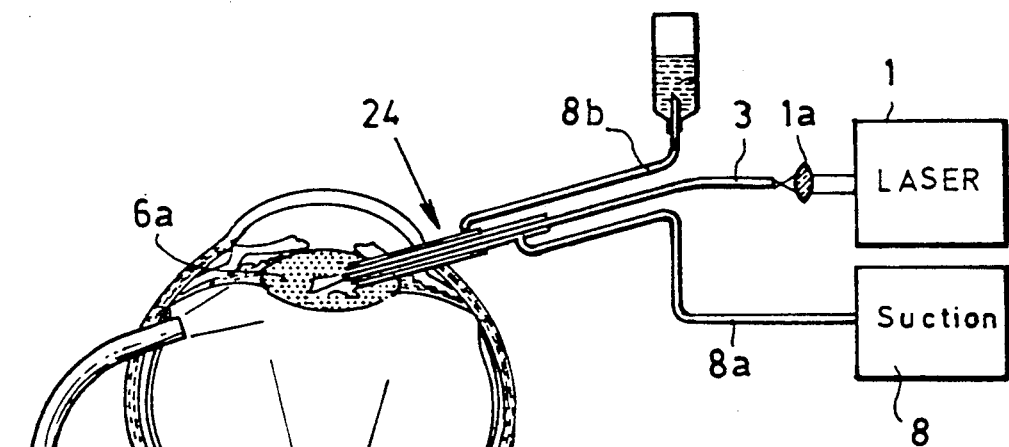
Fig. 6a
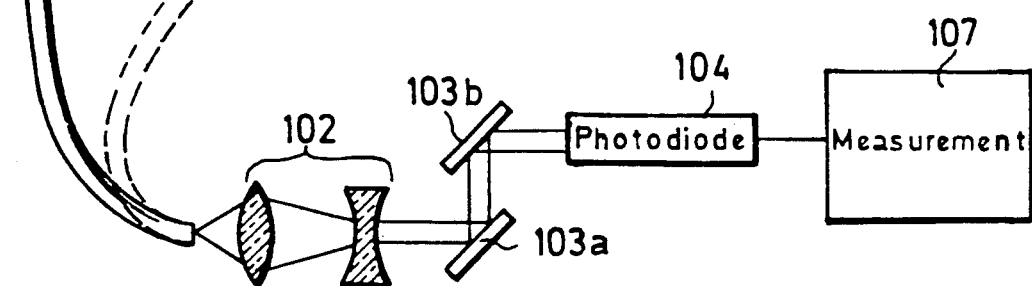

METHOD AND APPARATUS FOR PERFORMING SURGERY ON TISSUE WHEREIN A LASER BEAM IS APPLIED TO THE TISSUE

BACKGROUND OF THE INVENTION

Various suggestions have been made for removing biological tissue with the aid of photodecomposition (photoetching) by means of short laser pulses. Publications directed to this subject matter are listed below.

1. Health Physics Vol. 40, 1981, p. 677 to 683, Taboda et al: "Response of the corneal Epithelium to KrF Excimer Laser Pulses";
2. American Journal of Ophthalmology 96, 1983 p. 710 to 715, Trokel et al: "Excimer surgery of the cornea";
3. Ophthalmology 92, 1985, p. 741 to 748, Puliafito et al: "Excimer laser ablation of the cornea and lens";
4. Arch. Ophthalmology 103, 1985, p. 1741/1742, Krueger and Trokel: "Quantitation of corneal ablation by ultraviolet laser light";
5. Ophthalmology 92, 1985, p. 749 to 758, Marshall et al: "An ultrastructural study of corneal incisions induced by an excimer laser at 193 nm";
6. American Journal of Ophthalmology Vol. 103, p. 713 and 714, Berlin et al: "Excimer laser Photoablation in Glaucoma Filtering Surgery";
7. American Journal of Ophthalmology Vol. 99, p. 483 and 484, Pellin et al: "Endoexcimer laser Intraocular Ablative Photodecomposition";
8. Arch. Ophthalmology Vol. 104, 1986, p. 1825 to 1829 Nanevicz: "Excimer laser ablation of the lens".

Tissue removal with pulsed lasers at the eye is also the subject matter of U.S. Pat. Nos. 4,686,979 and 4,744,360.

The above publications and patents describe how corneal tissue, lenticular nuclei, scleral tissue in the iridocorneal angle, vitreous body tissue or tissue of the ocular fundus can be removed pursuant to the method of photoremoval with minimal thermal necrosis of the edges of the incision while utilizing excimer lasers at wavelengths of 193 nm and 308 nm. Finer incisions are possible with excimer lasers in this wavelength range than with Nd-YAG or CO2-lasers in the wavelength range between 1 $\mu$m and 10 $\mu$m. This is so not only because of the shorter wavelengths of the excimer laser, but also because of the basically different process of photodecomposition which is a threshold process as described in the publications and takes place only above a predetermined energy density in dependence upon the effective wavelength of the laser used.

When performing surgery on tissue by means of laser radiation, the difficulty always occurs to select the wavelength of the laser radiation so that the wavelength corresponds to the absorption characteristics of the tissue. If this match is not provided, then the energy density of the laser radiation required for tissue removal is to be selected high and then a relatively large thermal necrosis zone occurs along the incision edges.

Because of these difficulties, the tendency is to utilize different lasers for surgical incisions at different biological tissues or to operate at different wavelengths. This however requires a substantial effort.

SUMMARY OF THE INVENTION

It is an object of the invention to provide a method and apparatus for performing surgery on biological tissue by means of a laser beam wherein no radiation is needed which is adapted in its wavelength optimally to the tissue to be treated. It is a further object of the invention to provide such a method and apparatus which has a good efficiency and leads to relatively small necrosis zones along the edges of the incision.

According to a feature of the invention, a substance is applied to the tissue which is absorbant in the range of the laser wavelength and this substance is applied before or during the application of the laser beam.

The invention borrows from the unexpected result that it is possible to color the biological material to be removed with substances which are absorbant in the range of the laser wavelength in such a manner that, on the one hand, the effective threshold for the process of removal is significantly reduced and this is substantially independent of the absorption characteristics of the tissue itself. On the other hand, and likewise unexpected, the ablated volume per applied laser pulse clearly increases. At the same time, thermal necrosis zones on the edges of the incision are drastically reduced. This is a consequence of reduced temperature increase in the tissue because of the more effective removal process when the substance is applied before or during the laser treatment.

With the method of the invention, it is possible to operate with significantly lower energy densities than known up till now and recommended in the publications cited above.

The method of the invention is especially advantageous in its application to microsurgery on the eye. For this purpose, laser radiation is utilized having wavelengths in the ultraviolet spectral range, for example, at 308 nm or 193 nm. The tissue removal takes place in accordance with the method of photoablation. The photodecomposition occurring is a threshold process and takes place only above a predetermined energy density in dependence on the wavelength of the laser radiation used or the so-called effective threshold. By applying substances which absorb in the wavelength range of the laser radiation, the effective threshold is significantly reduced. On the other hand, the applied substance reduces the stray radiation and the fluorescence radiation in the eye so that the danger of cataract formation or retina damage is minimized.

If an opeation is performed at the wavelength of 308 nm, there is a risk of cataract induction if the operation is performed in the anterior portion of the eye. Also, there is the risk of retina damage if the operation is performed in the vitreous body or the eye lens is removed since the ocular media except for the lens are permeable to a great extent for the wavelength 308 nm. The application of the substance which is absorbant at 308 nm reduces the stray radiation of the laser wavelength in the eye which occurs during treatment; that is, the laser light is held away from the lens or the retina so that the danger of damage is very substantially minimized.

When operating at a wavelength of 193 nm, the disadvantage must be accepted that at the present time, no light-conducting fibers are available for transmitting the radiation to the location of the operation. Surgical procedures in the interior of the eye are therefore not possible without additional measures. The use of the wavelength 193 nm affords the advantage with respect to the wavelength of 308 nm that the thermal necrosis zones around the region actually to be removed can be held smaller by a factor of 20 to 50.

Notwithstanding this advantage, the wavelength of 193 nm has not been used for microsurgery on the eye since stray radiation or effective radiation of the laser not transformed in the process caused the danger of mutagenic changes of healthy tissue areas. New investigations have shown that the irradiation of the cornea with radiation at 193 nm effects the photoablation as well as the emission of shortwave fluorescence of the cornea as well as radiation emission based on the photoablation process. By increasing the energy density above the effective threshold, the shortwave component of this fluorescence radiation becomes larger in the spectrum. Wavelengths occur especially in the range of 290 to 320 nm. These wavelengths are transmitted by the cornea and absorbed by the lens because the cornea is permeable above 300 nm. Radiation in this wavelength range has a definite tendency to produce cataracts and is therefore especially dangerous for the eye lens.

If, according to the method of the invention, a UV-absorbing substance is applied to the site of the operation, then the intraocular structures are shielded from the dangerous wavelengths of the secondary radiation which occur, as described, with the photoablation of the cornea by means of 193 nm laser radiation.

The method of the invention makes possible for the first time the use of the especially efficient 193 nm laser radiation for the photoablation of the cornea without having to accept endangering intraocular structures caused by the occurring secondary radiation.

It has been shown that the ultraviolet-absorbing substances, which are used together with laser radiation at 308 nm, are also suitable for the required shielding when using laser radiation at 193 nm.

The use of an excimer laser radiating at 193 nm or 308 nm in combination with a drug which is absorbant in the UV-range has been shown to be especially advantageous. This drug contains a sulfonamide component absorbant in the UV-range such as sulfisomidine-sodium or sulfacetamide. Other suitable ultraviolet absorbing substance classes are: sulfonamides, tetracyclines, local anesthetics such as oxybuprocaine-HCl or tetracaine-HCl, beta blockers such as befunololhydrochloride, vitamins such as, for example, vitamin B or vitamin C.

Furthermore, substances such as indometacine, azetazolamide, para-amino-benzoic acid, pyridoxine-HCl, pyrimethamine, folic acid as well as a material known under the designation "Evans blue" are suitable for the above-mentioned purpose. All these substances contain aromatic ring systems which provide for ultraviolet absorption.

The used substance is absorbant in the range of the wavelength of the laser radiation and should be contained in a carrier liquid having a galenic characteristic which assures penetration into the organic tissue to which the laser radiation is applied. A good penetration capability however means at the same time that the applied absorbant substance diffuses again relatively quickly out of the region in which the surgical incision is made. For this reason, it is advantageous to operate the laser intermittently and to apply the absorbant substance each time anew in the time between laser pulses. This can, for example, be achieved in that the absorbing substance is metered via a metering unit to the irrigation liquid which is anyway required for many surgical procedures.

For the above reason, it is advantageous to provide an electronic unit in the apparatus according to the invention which controls the metering of the substance via the metering unit.

It is further advantageous to measure the fluorescence of the treated site during the laser treatment and to switch off the laser as soon as the measured values exceed or drop below predetermined limit values which have been selected with respect to keeping damage to the tissue as low as possible.

BRIEF DESCRIPTION OF THE DRAWINGS

The invention will now be described with reference to the drawings wherein:

FIG. 3a is a side elevation view, in longitudinal section, of a manipulator suited for the vitrectomy with the section view being along the axis of the light conducting fiber of the manipulator;

FIG. 3b is a radial section taken along the line IIIb–IIIb of FIG. 3a of the front end portion of the manipulator;

FIG. 3c is a section view taken along line IIIc–IIIc of FIG. 3a showing another view of the end portion of the manipulator;

FIG. 4 is a section view of the manipulator suitable for lens ablation with the section view being along the axis of the light-conducting fiber contained therein;

FIG. 6a is a schematic showing an experimental test set-up for determining the ultraviolet exposure of the retina during a lens ablation with the manipulator shown in FIG. 4;

FIG. 6b is a schematic which shows the procedure of vitrectomy (surgery on the vitrous body) with the manipulator of FIG. 3;

DESCRIPTION OF THE PREFERRED EMBODIMENTS OF THE INVENTION

Figure 1:
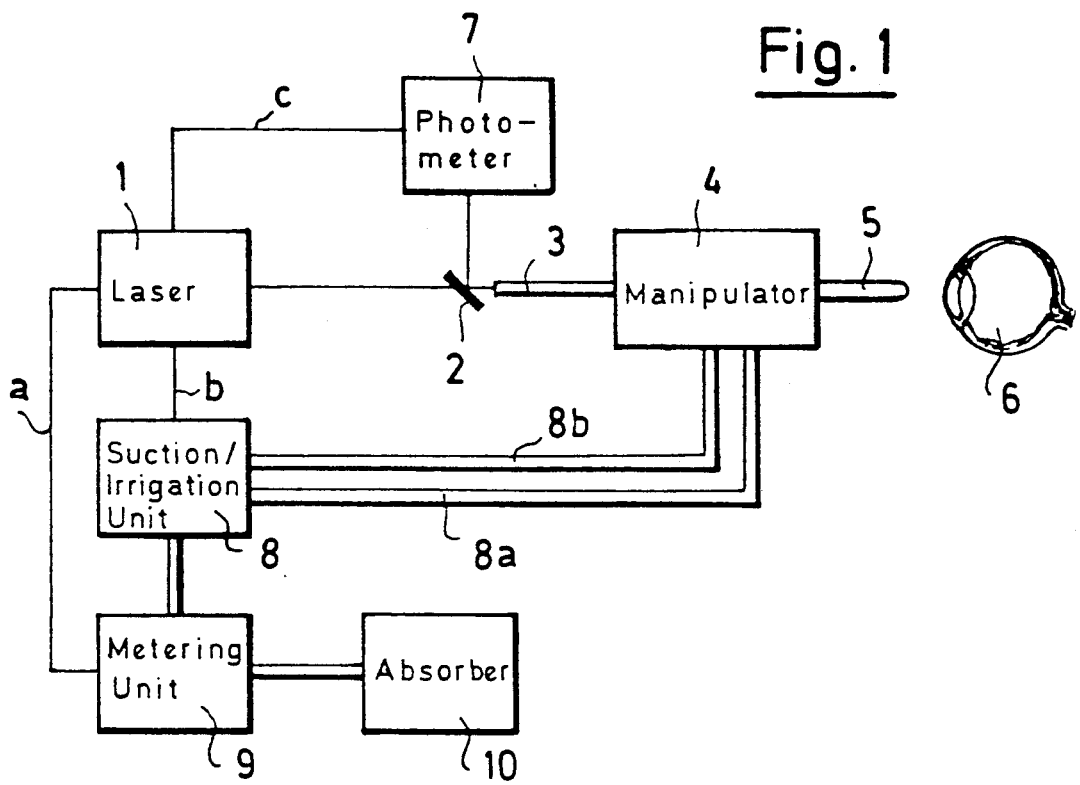
FIG. 1 is a schematic of the overall configuration of the apparatus according to the invention.

The apparatus shown schematically in FIG. 1 is for surgery on the eye by means of laser radiation. The apparatus includes a laser generator in the form of a xenon chloride excimer laser 1 which radiates at a wavelength of 308 nm and supplies pulse widths between 40 ns and 100 ns. The beam of this laser 1 is guided via a partially transmitting mirror 2 and focused on the end of a light-conducting fiber 3 made of quartz. This light-conducting fiber 3 is arranged in a manipulator 4 having a front end portion 5 where the end face of the fiber 3 facing toward the eye 6 terminates.

As will be described below, various manipulators (4, 5) are provided which are exchangeable in order to carry out the different surgical tasks on the eye.

A photometer 7 is mounted in the component beam path reflected out via the divider mirror 2. This photometer 7 measures the radiation backscattered from the eye, for example, stray radiation at the wavelength of the laser or fluorescence radiation. The photometer 7 is connected via a control output (c) with the laser generator 1 such that the laser can be switched off when the backscattered radiation drops below or exceeds predetermined limit values.

The manipulator 4 is connected via a system of suction lines 8a and irrigation lines 8b with a controlled suction/irrigation device 8 disposed in the laser base unit. A metering unit 9 is connected to the suction/irrigation unit 8 from which predetermined quantities of a substance are added intermittently to the irrigation liquid. The substance applied in this manner is an ultraviolet-absorbing substance and is stored in a supply vessel 10. In the same manner as the suction/irrigation unit 8, the metering unit is connected via control lines (a) and (b) with the laser generator 1 such that the laser 10 is shut off during the application of the absorbing substance and is again switched on after a predetermined time delay. In a further embodiment, the laser, the suction/irrigation unit 8 and the metering unit 9 can all be controlled by a computer or microprocessor.

The operation of the apparatus described above and the method for carrying out operations therewith such as a glaucoma operation, vitrectomy, removal of the lens nucleus and refractive corneal surgery will be described in connection with Examples 1 to 4 below.

EXAMPLE 1

The first example is directed to a fistulating glaucoma operation in the iridocorneal angle.

With this method, a channel is made between the anterior chamber and the subconjunctival chamber in the eye. This operation is more generally referred to as "sclerostomy". Synonymous herewith, the name "gonioablation" can be used if an excimer laser is used to perform this surgery.

Figure 5:
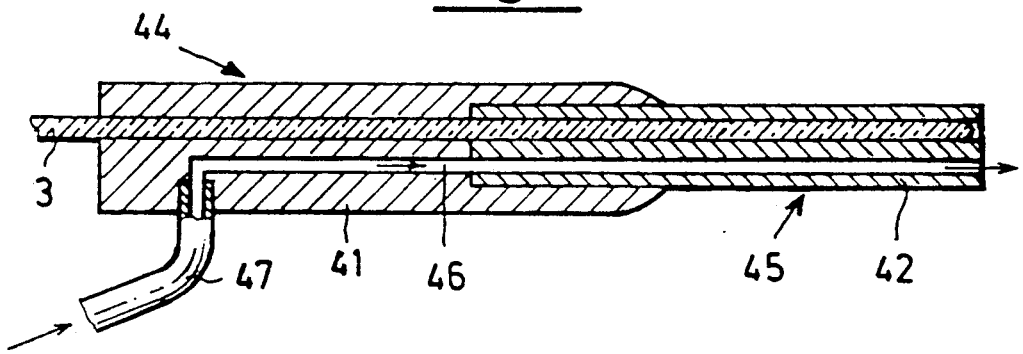
FIG. 5 is a section view of a manipulator suitable for goniopuncture taken along the axis of the light-conducting fiber contained in the manipulator.

The manipulator used for this surgical operation is shown in FIG. 5. The manipulator includes a handle 44 which extends at its forward end into a metal holder 45 having a thickness of approximately 1 mm. The quartz fiber 3 and an irrigation channel 46 are embedded in this metal holder 45. The irrigation channel 46 opens into a connection stub 47 in the handle and exits from the holder 45 at the other end face thereof.

Figure 2A:
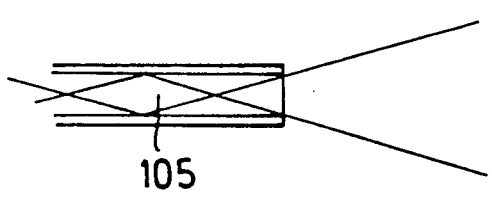
FIG. 2a is a schematic representation of fibers which have the highest energy density concentrated directly on the surface of the fibers.
Figure 2B:
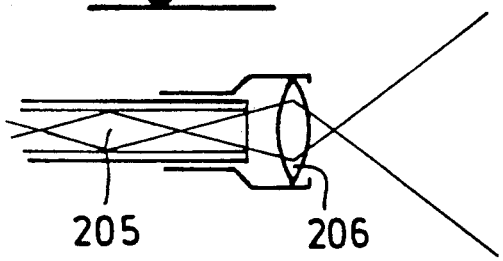
FIG. 2b is a schematic representation of a convex lens in a holder ahead of the fiber.
Figure 2C:
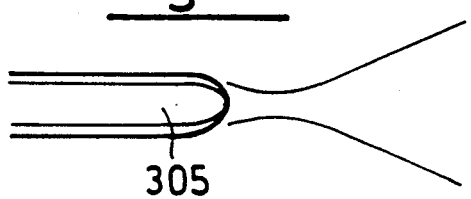
FIG. 2c is a schematic representation of a fiber having a convexly rounded end face.

The end face 305 of the fiber 3 has focusing characteristics and is therefore convexly rounded as shown in FIG. 2c. This configuration assures that the highest energy density is localized at approximately 1 mm ahead of the fiber tip. This makes it possible to make incisions without contact. Fibers having a planar end face 105 were used for this purpose up to the present time. In contrast to the configuration of FIG. 2c, the fibers of FIG. 2a have the highest energy density concentrated directly on the surface of the fibers so that no effective contactless incision is possible and the danger of a premature destruction of the fiber tip is present. Although a solution to this problem has already been suggested in that a convex lens 206 is provided in a holder ahead of the fiber 205 as shown in FIG. 2b. However, the diameter of the fiber tip is enlarged which in many cases is a hindrance and makes the introduction of the manipulator difficult.

Experiments were conducted on isolated eyes of pigs and sheep with an excimer laser beam at 308 nm with the laser beam coupled in via a quartz fiber in the anterior chamber. In these experiments, a fistula was made in the region of the trabecular system between the anterior chamber and the chamber beneath the sclera without the sclera being injured thereby. In order to hold the anterior chamber in a fixed position during the intraocular operation, the initial experiments were carried out with an anterior chamber infusion with the input being made at the limbus. The pressure present during the gonioablation in the anterior chamber was varied by the elevation of the infusion bubble.

Figure 6C:
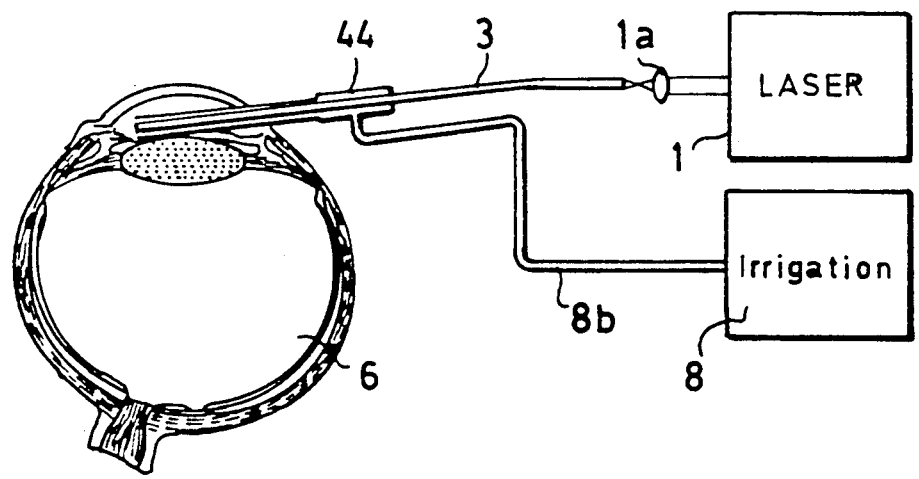
FIG. 6c is a schematic illustrating the procedure of gonioablation (fistulating glaucoma operation in the iridocorneal angle) utilizing the manipulator of FIG. 5.

FIG. 6c is a schematic showing the gonioablation being performed with a manipulator of FIG. 5. After opening the eye at the limbus with a dissection needle, the tip 45 of the manipulator 44 is introduced into the anterior chamber and pushed into the opposite-lying iridocorneal angle of the eye 6. During the time that minimum pressure is applied to the manipulator, the laser 1 is switched on and is focused via the lens 1a onto the rearward end of the quartz fiber 3. Gas bubbles develop in the iridocorneal angle from the action of the laser radiation. The instant of perforation in the region of the corneoscleral transition can be felt with a suitable manipulation. After the manipulator is withdrawn, a drainage system is spontaneously formed and the gas bubbles developed during the gonioablation rise into the anterior chamber.

The collapse of the anterior chamber is prevented by the irrigation channel in the manipulator 44 which is connected via the irrigation line 8b to a suction/irrigation unit 8.

The sclerostomy described above was not only carried out with an excimer laser but also for comparative investigations, with an argon laser at 488 nm and 514 nm as well as with a continuous Nd-YAG laser at 1064 nm. The histological investigation of the operated eyes shows that necrosis widths between 300 μm and 700 μm resulted for the Nd-YAG laser (applied power 20 to 40 watts at 0.1 seconds pulse width) as well as for the argon laser (applied power 0.3 to 3 watts at pulse widths between 0.02 and 1 second). In contrast thereto, the fistular channels generated with the excimer laser at wavelengths of 308 nm result in a necrosis zone having a width of only 40 to 60 μm. The pulse energy of the excimer laser was between 2 mJ and 10 mJ at a repetition rate of 20 Hz.

The width of this necrosis zone was reduced to a fifth when an ultraviolet-absorbing drug was introduced into the irrigation liquid before the laser was switched on. At the same time, the number of the necessary laser pulses was reduced and thereby the applied total energy was reduced by half. Such a drug is, for example, sulfisomidine-sodium 1 $H_2O$ 114.4 mg/ml corresponding to 100 mg/ml sulfisomidine. In the following, this substance is referred to as "substance A" and is offered for sale in Europe under the trade name "Aristamid".

Another suitable drug containing ultraviolet-absorbing substances are eye drops which are offered for sale under the designation "Blephamide Liquifilm". This drug is designated in the following as "substance B" and is made up of sulfacetamide-sodium 105 mg per ml, prednisolone-21-acetate 2.2 mg per ml, phenylephrinhydrochloride 1.2 mg per ml, phenanzone 1.0 mg per ml and polyvinylalcohol as carrier substance 14.0 mg per ml. Sulfacetamide is contained herein as the effective ultraviolet-absorbing component.

EXAMPLE 2

This example is directed to a vitreoablation wherein a vitrectomy is performed with an excimer laser via a glass fiber.

The manipulator shown in FIGS. 3a to 3c is used to perform this surgical procedure. It is configured similarly to the manipulator for gonioablation shown in FIG. 5 and includes a handle 14 which extends into a metal tube 12 at its forward end. The metal tube is thin and has a thickness of approximately 1 mm. The quartz glass fiber 3 is held in one of the two channels in the manipulator 14 arranged one atop the other; whereas, the other channel 16 is configured as a suction channel and opens into a suction line 17. The fiber 3 is so attached in the manipulator that its tip is somewhat spaced back from the upper opening of the suction channel 16 in order to avoid contact of tissue drawn off by suction with the surface of the fiber. Furthermore, the metal holder 12 of the tip 15 of the manipulator carries a shielding diaphragm 13. This diaphragm 13 shields the retina against laser radiation exiting axially from the fiber.

During the vitrectomy, the vitreous body is drawn by suction through the lateral opening 18 between the diaphragm 13 and the end of the fiber 3 and is cut by the laser focus lying approximately in the suction channel. The cut vitreous body tissue is drawn off by suction through the suction channel 16. The suction opening for the vitreous body must be less than the beam of the excimer laser exiting from the fiber 3 so that only cut vitreous body tissue is drawn by suction since otherwise a blocking of the suction channel will result.

At the same time, the suction channel 16 or the infusion channel, which is anyhow available for a vitrectomy, function to intermittently apply UV-absorbing substances which reduce the ablation threshold of the vitreous body tissue and shield the remaining eye tissue, especially the retina from ultraviolet stray radiation.

In initial experiments, it was shown that the vitreous body tissue can be cut with the excimer laser at 308 nm and the manipulator shown in FIG. 3. At the same time, measurements of the ablation rate for vitreous body tissue were carried out. An isolated vitreous body was ablated in a cuvette and suction applied thereto. The ablation rate was determined from the difference of the weight of the specimen before and after the ablation. A value of 5 mJ/mm$^2$ was obtained as the threshold for the vitreous body ablation. The ablation rates determined for a repetition rate (pulse frequency of the laser) of 20 Hz lie in the range of 200 mg/min at a pulse energy of 15 mJ for a fiber having a thickness of 600 μm and as used in the manipulator of FIG. 3.

If an UV-absorbing substance is first applied to the vitreous body, a drastic increase of the ablation rate to a value of over 1 g/min was obtained. An effective shielding of the retina during the vitreoablation is also provided because of this increase of the UV-absorption of the vitreous body.

FIG. 6b is a schematic showing the procedure of a vitreoablation during an operation. If the vitreoablation is so carried out, then it is advantageous to work with a manipulator which has a bent-over tip as shown in FIG. 6b. This permits removal of the vitreous body on the vitreous body base without inducing the formation of a cataract by touching the posterior lens surface.

The UV-absorbing drug is applied through the suction channel 16 of the vitrectomy manipulator 14 intermittently with respect to the suction/cutting operation. This is achieved by means of an appropriate control of the suction/irrigation unit 8.

EXAMPLE 3

This example is directed to an endocapsular phacoablation using an excimer laser via a quartz fiber.

The manipulator 24 for this procedure is shown in FIG. 4 and includes a cylindrical handle 31 on which a suction stub 27 is mounted. A cannula shaft 21 is mounted in the rearward end of the cylinder 31 into which an irrigation line 29 opens. The forward end of the cannula shaft 21 holds a cannula tube 28 in its interior which separates the inner suction channel 32 from an outer suction channel 26. The suction channel 26 is formed by a second cannula tube 22 disposed coaxially about the inner cannula tube 28 and is mounted in the forward end of the handle 31. In addition, the glass fiber 3 is held inside the irrigation channel. The forward rounded focusing end of the glass fiber 3 is set back approximately 1 mm behind the tip of the manipulator 24. The fiber is continuously irrigated with a solution in order to keep the ablation products away from the fiber tip. The drawing off by suction of the lens fragments takes place via the suction channel 26 which is concentrically guided about the irrigation channel 32.

The endocapsular phacoablation was achieved with this manipulator with only minimal damage to the capsule of the lens. The process is explained with reference to FIG. 6a. The opening in the capsule of the lens 6a is made pursuant to a method described in the literature with the aid of a thermocautery. The manipulator 24 and the quartz glass fiber integrated therein is pushed into the lens 6a through this opening. First, the cortex lying ahead of the nucleus is ablated and drawn off by suction. Thereafter, the ablation of the nucleus takes place. After complete ablation and drawing off by suction of the nucleus, the cortex is drawn off by suction in a conventional manner. The empty capsular bag was filled with an optically transparent gel (methylcellulose) for controlling the result.

In order to determine how intensely the retina was stressed with UV-radiation during the phacoablation, the UV-radiation reaching the retina was measured during the operation in an experiment on an isolated steer eye. In the region of the macula and in the region of the peripheral retina, a 1 mm thick quartz glass fiber 101 was placed and the UV-radiation received thereby was bundled through a Galilei telescope 102 and imaged on a photodiode 104 via two dielectric mirror (103a, 103b) which reflect only the wavelength 308 nm of the laser 1. The photodiode 104 was connected to a calibrated energy measurement device 107. This arrangement assured that the light of the operating microscope as well as the inherent fluorescence of the lens occurring during ablation of the lens was not measured.

In the area of the macula as in the peripheral retina, the energy density measured during the phacoablation was significantly less than the threshold for retina damage which lies at 5 $J/cm^2$ for the wavelength 308 nm. A further drastic drop in the energy density on the retina was achieved by means of an intermittent application into the irrigation liquid of the above-mentioned UV-absorbing drugs (substance A or substance B). Experiments on eyes obtained from a slaughter house have shown that even with a drop application of the UV-absorbing substance on the cornea, an adequate concentration in the vitreous body of the eye 6 was obtained in order to effectively shield the retina against stray radiation of the laser at a wavelength of 308 nm.

EXAMPLE 4

This example is directed to refractive corneal surgery with an excimer laser at 308 nm via a glass fiber.

Figure 7:
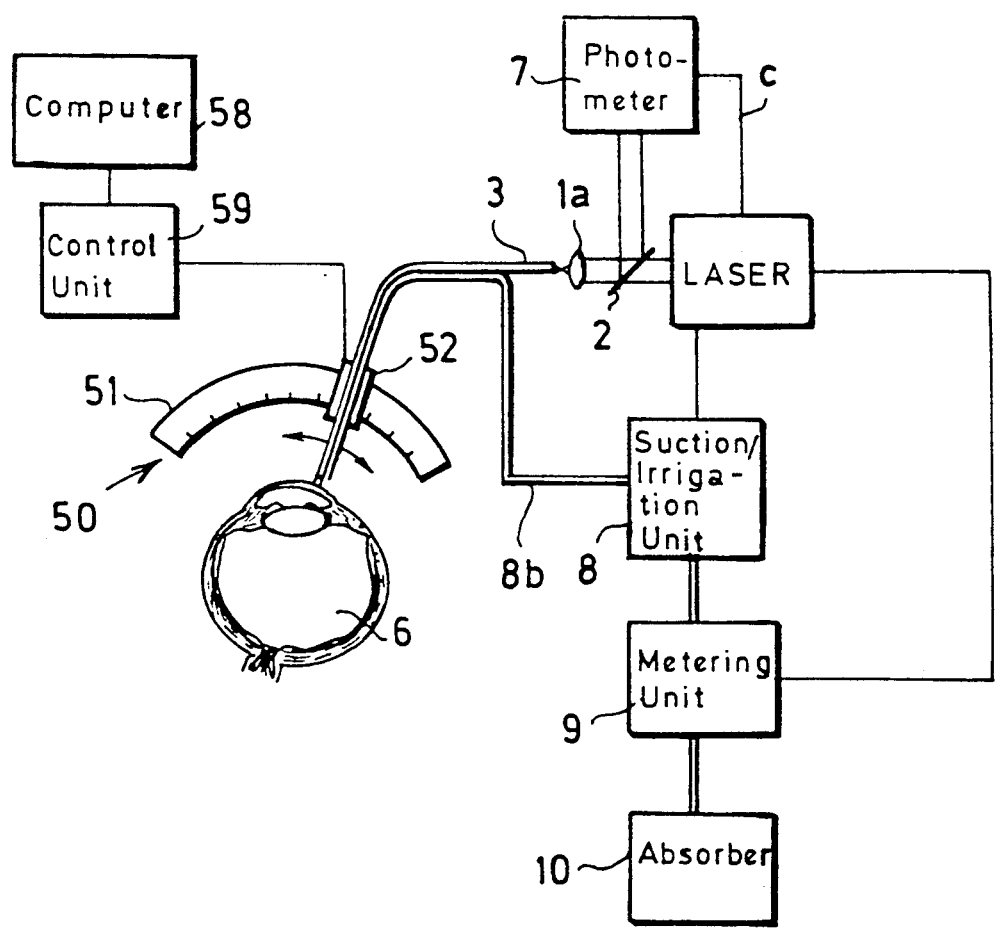
FIG. 7 is a schematic showing the overall configuration of the apparatus according to the invention in combination with a eucentric micromanipulator for corneal surgery.

This operation is shown in the schematic of FIG. 7 and a eucentric micromanipulator is additionally used for this operation. With the aid of the micromanipulator, the geometry of the cornea in diverse incision directions can be tracked and reproduced after the spatial curve for the incision is programmed into the computer. Such micromanipulators are known per se and comprise an arcuate guide 51 on which a carrier 52 is guided and which is electrically driven and positioned. A computer 58 as well as a control unit 59 connected in cascade with the computer are provided for the positioning.

The quartz glass fiber 3 and an irrigation tube are held in holder 52 with the irrigation tube being configured in the manner of the tip 45 of the manipulator 44 shown in FIG. 5. In this way, the beam of the excimer laser 1 is guided concentrically to the curvature of the cornea so that it passes over the latter. The beam of the excimer laser 1 is coupled into the fiber 3 via the optic 1a. The suction/irrigation unit 8 corresponds to that shown in FIG. 1 and is again connected via a metering unit 9 to a supply vessel 10 wherein one of the above-mentioned substances (substance A or substance B) is stored. In addition to metering the substance, the irrigation line 8b applies moisture to the cornea with a physiologic saline solution during the operation.

Fluorescence radiation is backscattered from the cornea and transmitted back via the fiber 3. A photometer 7 is provided which measures this fluorescence radiation after it is coupled out via the divider mirror 2 and switches off the laser generator 1 via the control line (c) when a fluorescence signal which is too high indicates an inadequate concentration of the UV-absorbing substance in the cornea.

Corneas of pigs and sheep were irradiated until perforation occurred to determine the ablation rate. The number of laser pulses required for this purpose were counted. Measurements of the thickness of the cornea center with an electronic slide gauge as well as with a microscope having an eye piece scale resulted in good reproducibility for a cornea thickness of 0.7 mm which provided the basis for the investigation. The ablation rate was determined from the number of laser pulses required to achieve the perforation of a cornea.

Figure 8:
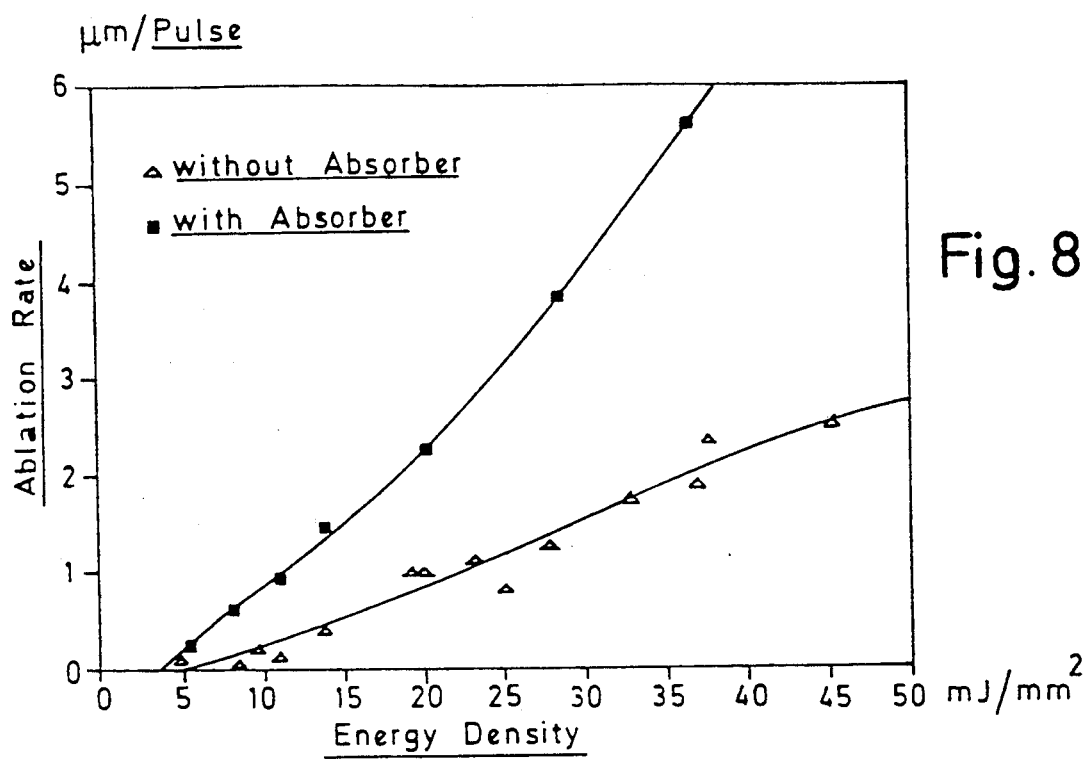
FIG. 8 is a graph showing the ablation rate on a cornea of a pig versus energy density with and without the application of absorbing substances.
Figure 9:
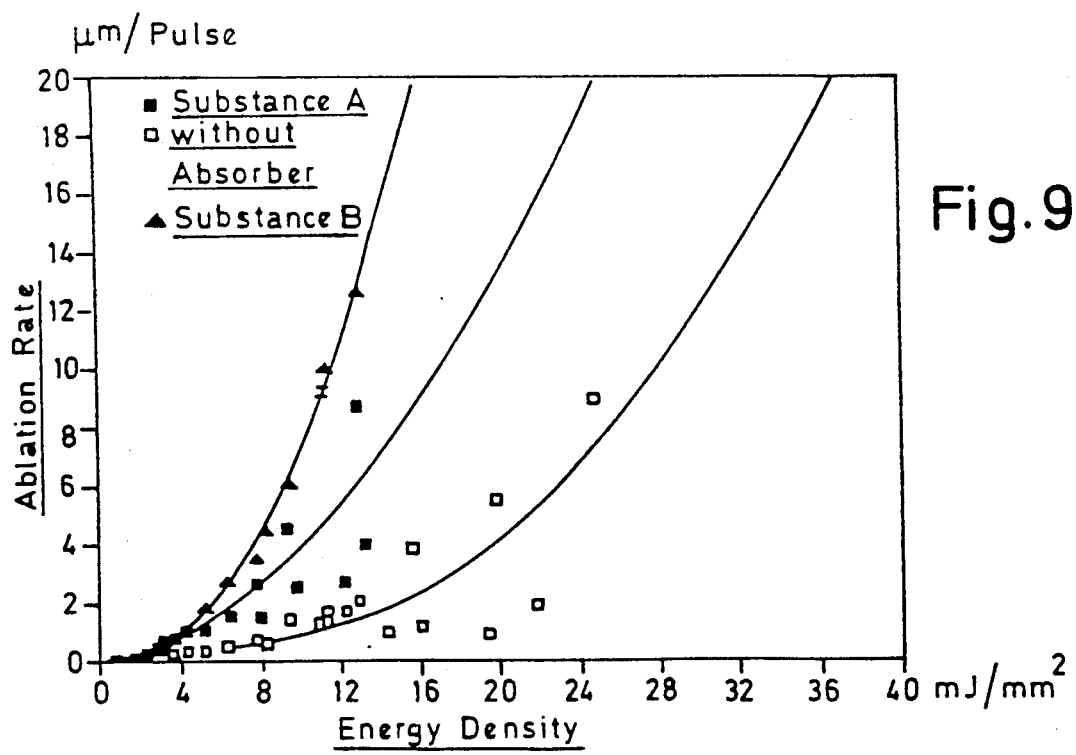
FIG. 9 is a graph showing the ablation rate on a sheep cornea versus energy density with and without the application of absorbing substances.

With the measurement of the ablation rates while using a suitable UV-absorbing substance, it was shown that all absorbers mentioned initially reduced the ablation threshold and significantly increased the ablation rate. For this purpose, reference can be made to the diagrams of FIGS. 8 and 9. The diagram of FIG. 8 was determined on a pig cornea at a wavelength of 308 nm; whereas, the ablation curve of FIG. 9 shows sheep corneas with and without UV-absorbers. In both cases, the ablation rate in micrometers per pulse is shown plotted against the energy density per laser radiation for a fiber tip in mJ per square millimeter. The diagrams show that by applying the above-mentioned substances A and B, the ablation rate is very greatly increased and in some instances more than by a factor of 2 and, furthermore, the ablation threshold is lowered, that is, the energy density after which ablation only first occurs. Accordingly, the application of the absorbing substance permits operating with a reduced energy density and yet enables the operation to be shortened whereby the ultraviolet exposure of the eye tissue is significantly reduced.

Figure 14:
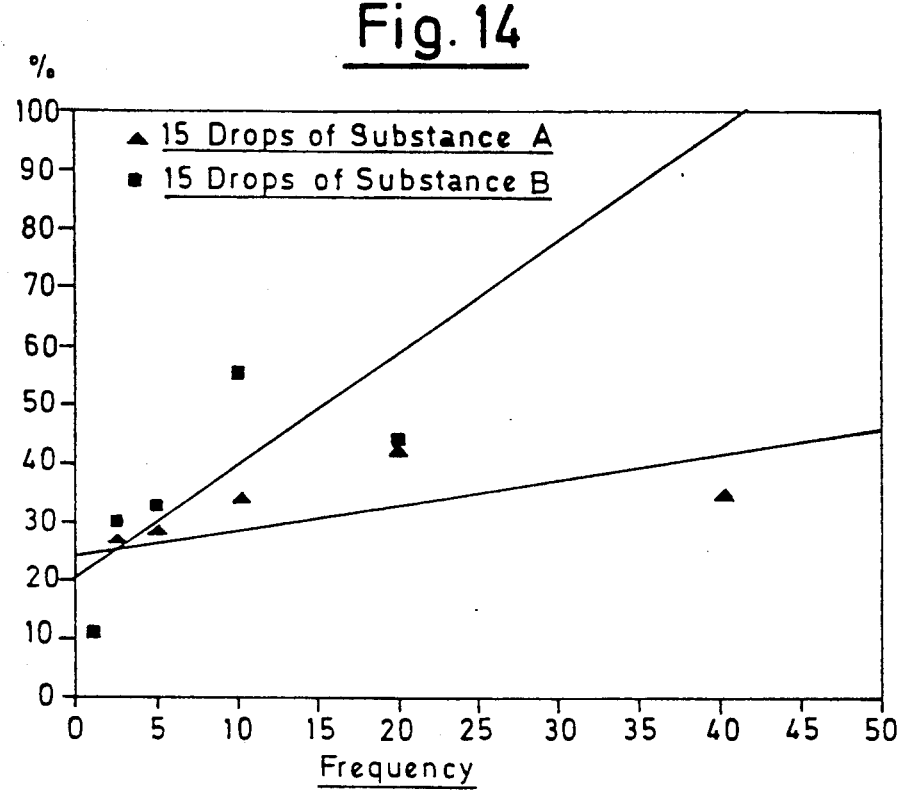
FIG. 14 is a diagram showing the dependence of the depth of the incision through the cornea on the repetition rate of the laser used with the application of various ultraviolet-absorbing substances.

The incision depth per pulse is a function of the pulse rate used and this is shown in FIG. 14. In FIG. 14, the incision depth into the cornea in percent of the cornea thickness effected by 100 laser pulses is plotted against the repetition frequency of the laser in Hz. From FIG. 14, the higher effectivity of the substance B can be recognized which, with 100 laser pulses at a repetition rate of 40 Hz, makes possible incisions through the entire cornea thickness.

Figure 10:
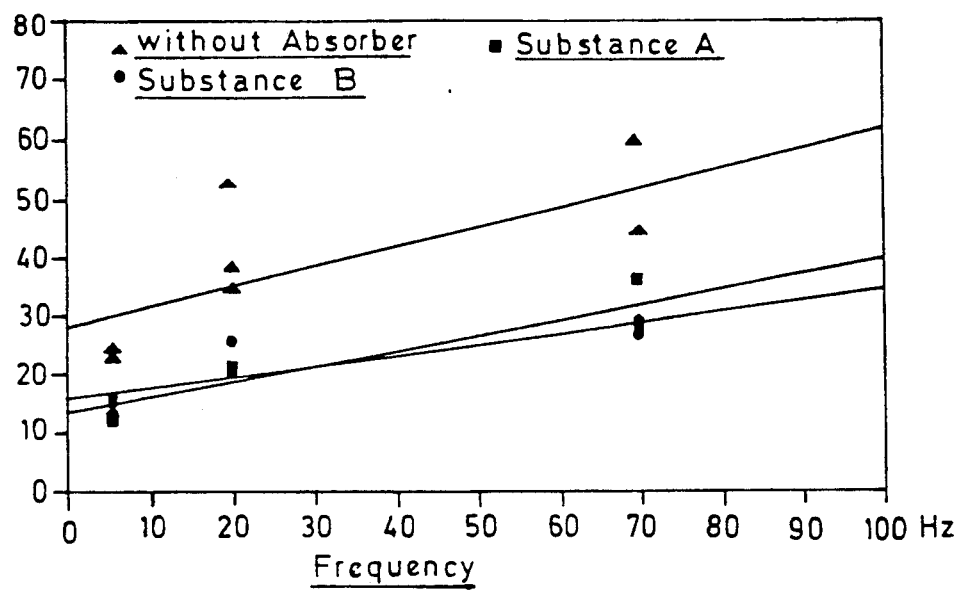
FIG. 10 is a diagram showing the increase in temperature in the cornea in dependence upon the repetition rate of the laser used with and without the application of various ultraviolet-absorbing substances.

At the same time, the substance A as well as the substance B reduce the increase in temperature in the cornea which takes place during the incision. This is clearly shown in the diagram of FIG. 10 wherein the temperature increase in degrees is plotted against the repetition rate of the laser in Hz for corneas of sheep untreated and after the substance B and the substance A have been applied in respective time durations of five minutes over a time span of one hour.

Figure 11:
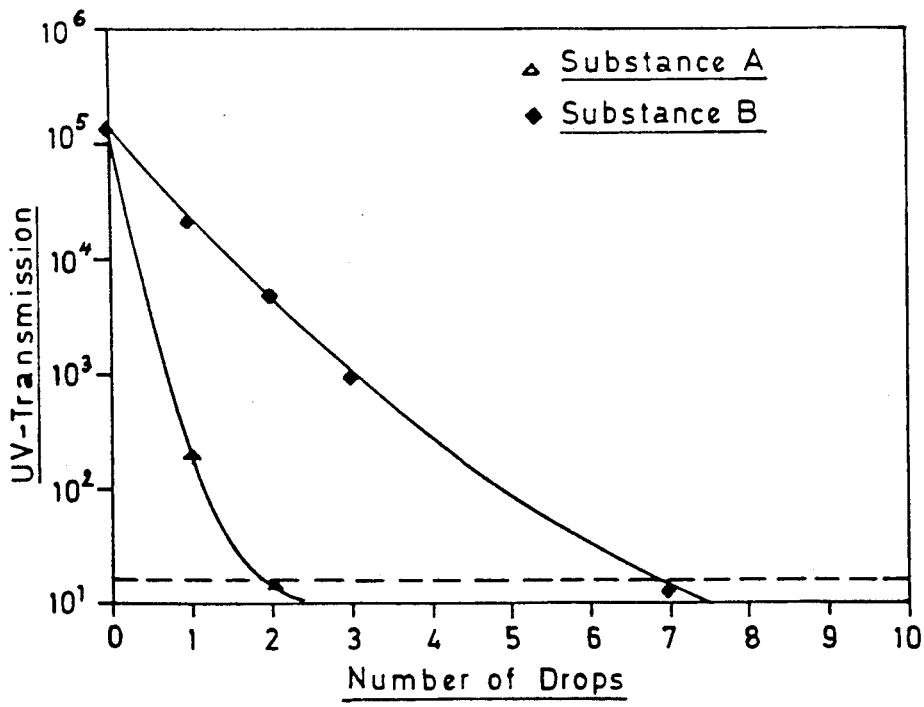
FIG. 11 is a diagram showing the dependence of the radiation at 308 nm, which is transmitted through the cornea, on the number of drops of various ultraviolet-absorbing substances.

In addition, the eye lens is effectively shielded from the radiation of the laser at the wavelength of 308 nm by the applied UV-absorber such as substance A and substance B. This result was confirmed in a quantitative measurement. For this purpose, a 1,000 μm thick fiber was pushed from the rearward pole of the eye through the vitreous body and the lens of sheep eyes into the anterior chamber. In FIG. 11, the UV-transmission of the cornea treated with substance A and B and measured by an optical multichannel analyzer via the fiber is shown as a function of the number of drops of the substance. This diagram shows that few drops are already adequate in order to drop the UV-light transmitted through the cornea so that it is below the detection limit.

Figure 12:
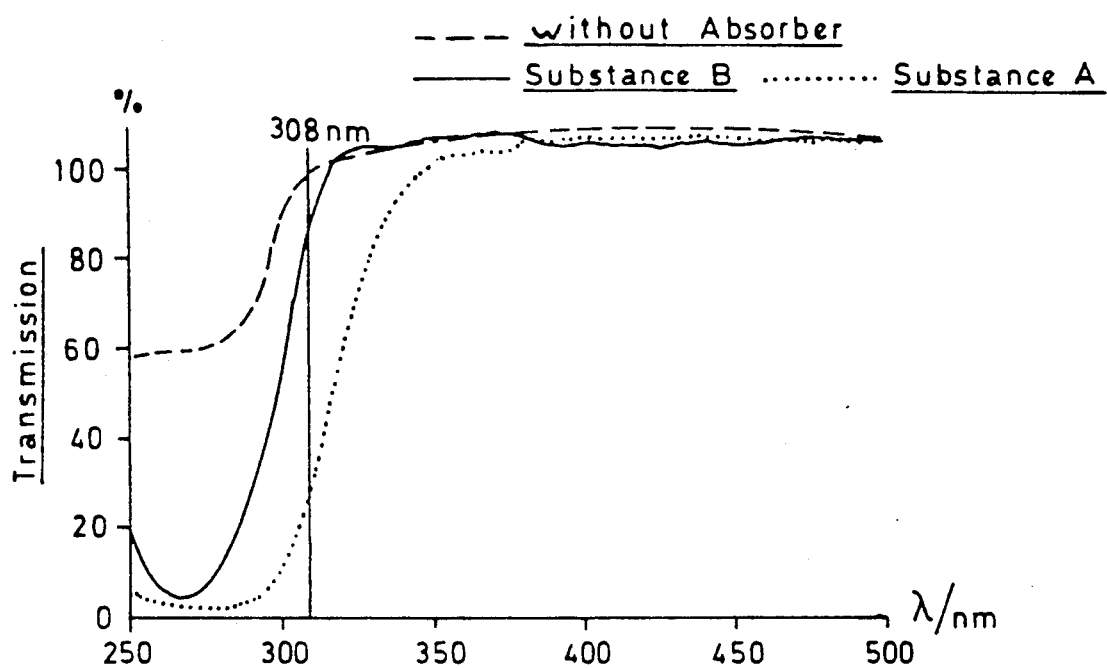
FIG. 12 shows transmission spectra of 10 μm thick corneal discs which have not been treated and those which have been treated with eight drops of various ultraviolet-absorbing substances.

This result is easily correlated with the corresponding absorption spectra of 10 μm thick cornea discs which have been treated with the appropriate substances. These spectra are shown in FIG. 12 and show that in a wavelength range of under 340 nm, the transmission of the corneas treated with substances A or B is significantly less than the transmission of untreated corneas.

Furthermore, an improvement in the quality of the incision effected by the UV-absorber can be shown from histologic investigations. Histologic incisions of a laser incision carried out with 1 J/cm$^2$ in an unmodified cornea produce necrosis zones having a width of approximately 200 μm directly at the edges of the incision in which vacuoles are also found. A wide zone of approximately 500 μm extends from this zone of necrosis with a loosening of the structure. At lower energy densities beneath the threshold, no incision results and instead, only a similar zone of necrosis with vacuoles occurs. If an eye treated with substance A is irradiated with the same energy density, an incision again results for an unmodified cornea beneath the threshold energy density. The zone of necrosis at the edges of the incision amounts to only 2 to 5 μm.

Figure 13:
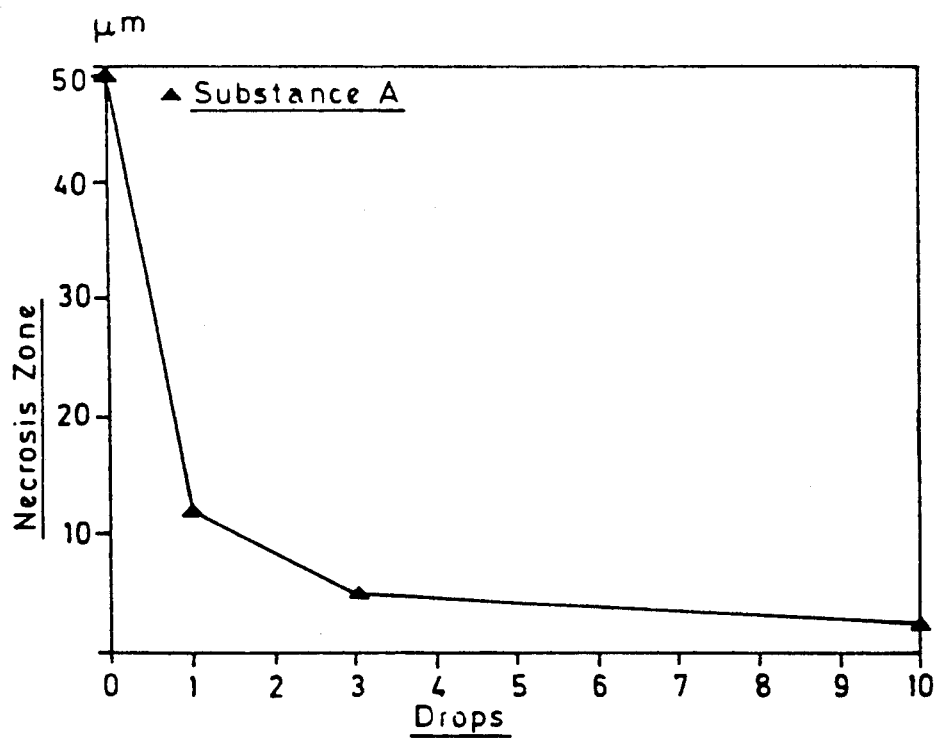
FIG. 13 is a diagram showing the dependence of the width of the necrosis zone of a cornea pretreated with an ultraviolet-absorbing substance upon the number of applied drops shown.

The dependence of the necrosis width on the number of drops of the substance used is shown in FIG. 13. Already with a few drops, the substance A permits the width of the zone of necrosis to drop by more than one order of magnitude. In contrast, an increase of the number of drops above three drops effects no drastic change.

The time between the application of the drops and the switch-on of the laser must not be too long since the cornea concentration of the UV-absorber reduces because of diffusion into the interior of the eye after longer delay times. This can be advantageously avoided by introducing the substance into the irrigation line integrated into the manipulator so that the substance can be metered as required. This makes an intermittent operation of the apparatus necessary.

Figure 15:
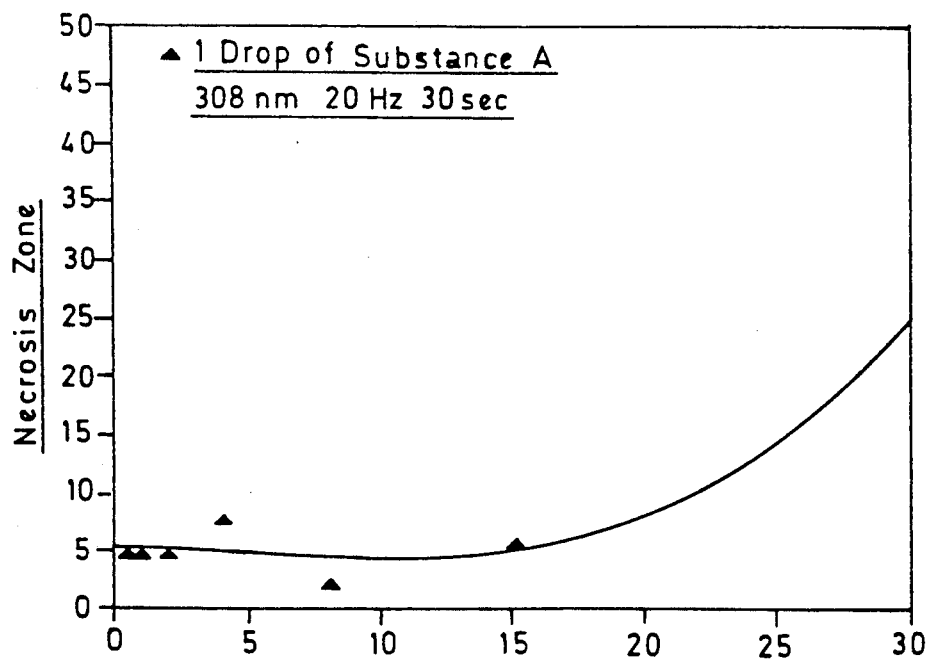
FIG. 15 is a diagram showing the width of the necrosis zone of a cornea pretreated with an ultraviolet-absorbing substance from the time between drop application and the beginning of the laser treatment.

The maximum delay time between applications of the substance and the beginning of the laser incision can be determined experimentally. For this purpose, various incisions at different time intervals have been carried out after the substance is applied and the width of the zone of necrosis after each incision is determined. The result is shown in FIG. 15. For delay times exceeding 15 minutes, the width of the zone of necrosis increases since the UV-absorber (substance A) diffuses out of the cornea and into the eye interior.

The corneal surgery described with respect to Example 4 can be carried out also with an excimer laser emitting at 193 nm, for example, an argon fluoride laser. The fiber 3 shown in FIG. 7 is replaced with an optical system of a known kind because the wavelength cannot be conducted through a light-conducting fiber at this time. The optical system focuses the radiation emanating from the laser source onto the cornea of the eye 6. With a movement of the focused laser spot across the cornea, the laser can be moved therewith or, a mirror arrangement can be provided by means of which the laser light follows the moved optical system.

Figure 16:
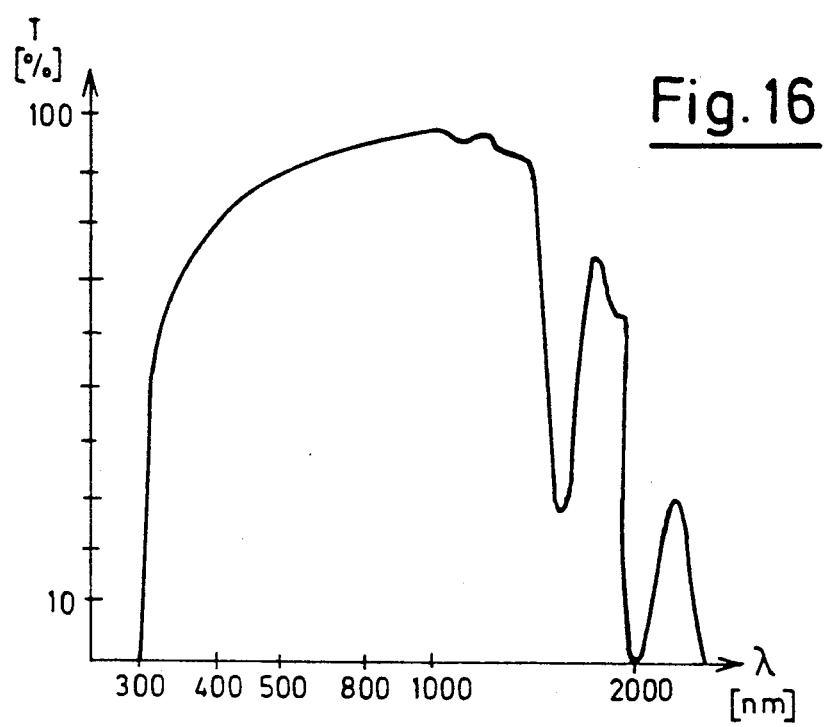
FIG. 16 shows the transmission spectrum of a cornea.
Figure 17A:
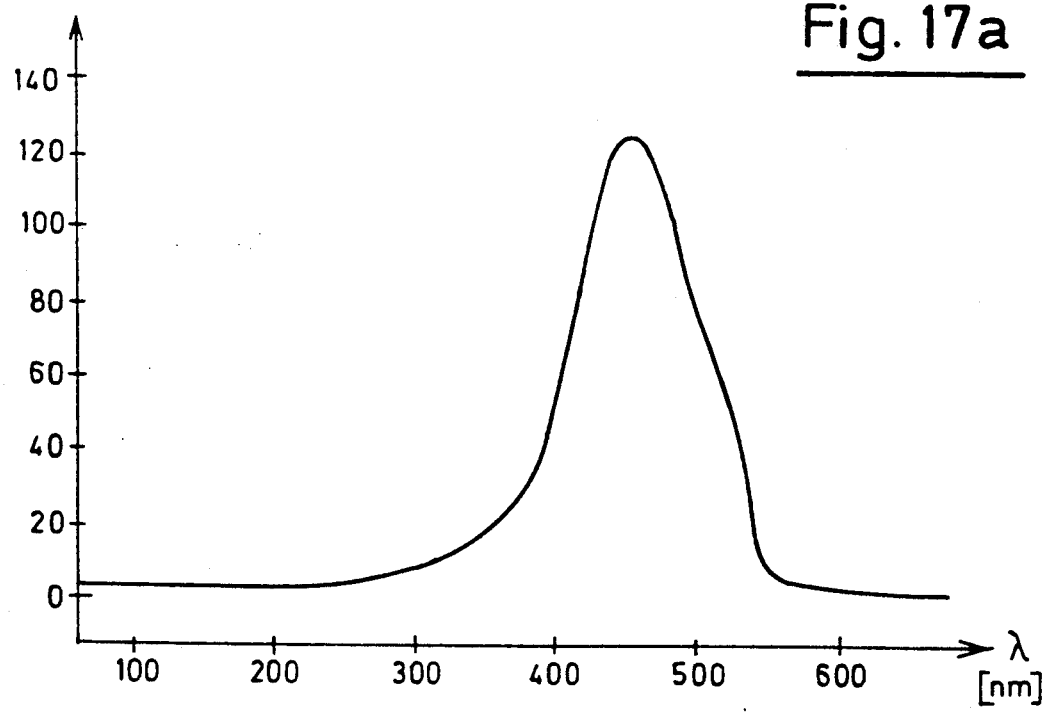
FIG. 17a shows the spectrum of the fluorescence radiation transmitted into the interior of the eye and occurring during the radiation of the cornea with a 193 nm laser radiation below the effective threshold.
Figure 17B:
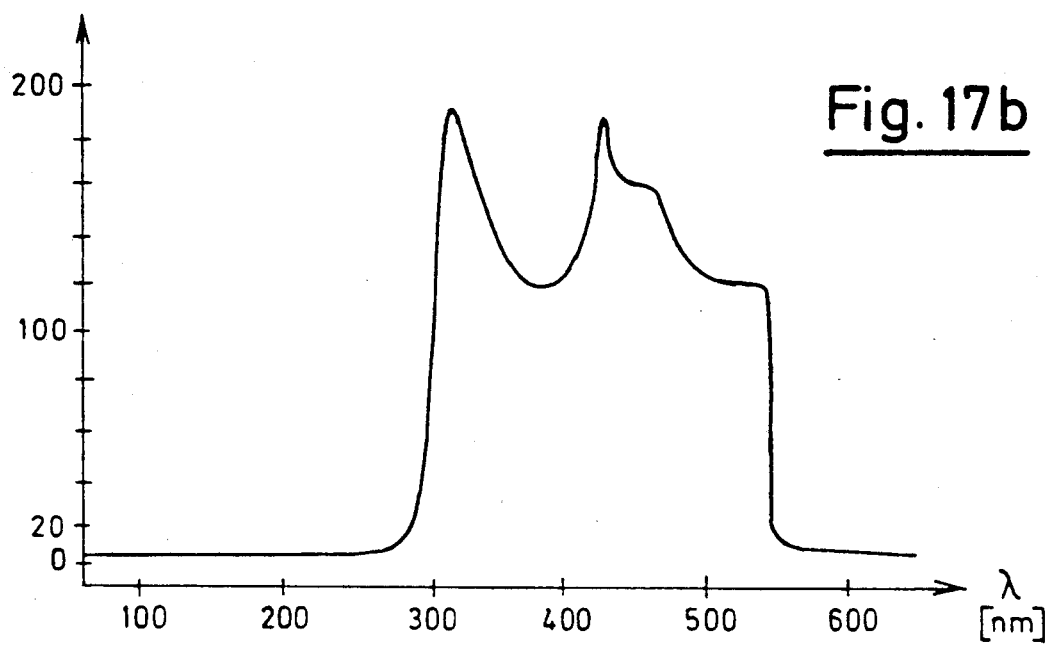
FIG. 17b shows the spectrum of the fluorescence radiation transmitted into the interior of the eye and occurring during radiation of the cornea with 193 nm laser radiation above the effective threshold; and, FIG. 18 shows the spectrum of the fluorescence radiation transmitted into the interior of the eye and occurring during irradiation of the cornea with radiation at 193 nm above the effective threshold on a cornea pretreated with an ultraviolet absorber.

As shown in FIG. 17a, a fluorescence radiation is triggered with an irradiation of the cornea with a laser beam at 193 nm which reaches the interior of the eye in correspondence to the transmission curve of FIG. 16. If in contrast to FIG. 17a, the energy density of the laser radiation is increased above the effective threshold so that photoablation is effected, the shortwave component of the secondary radiation becomes greater in the spectrum as shown in FIG. 17b. Since the cornea is transparent above 300 nm, this shortwave radiation is passed through and absorbed by the lens. Investigations have shown that wavelengths between 290 and 320 nm are especially dangerous for the lens because of their capability to cause cataracts. The threshold for generating cataracts with this wavelength lies at approximately 600 mJ/cm$^2$.

Figure 18:
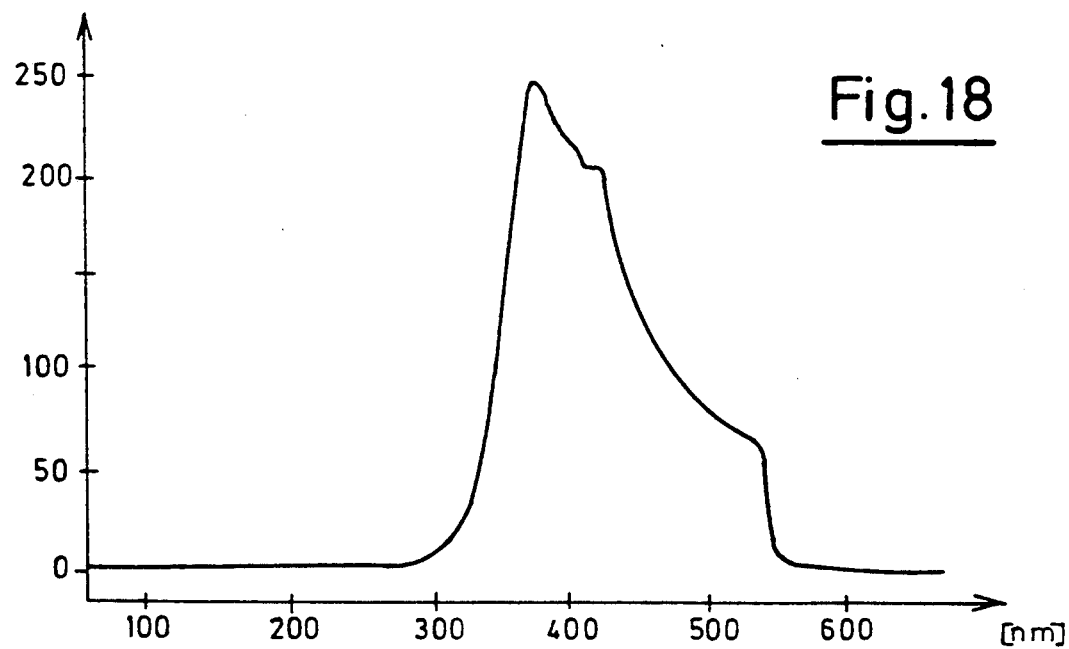

FIG. 18 shows the situation when an UV-absorbing substance such as oxybuprocaine is applied to the cornea on which the laser beam impinges. This can occur, for example, via the irrigation line 8b of FIG. 7.

FIG. 18 shows that the damaging secondary radiation between 290 and 320 nm is almost completely absorbed and therefore does not occur any more in the spectrum.

In this way, the laser radiation of the wavelength of 193 nm can be used for corneal surgery without endangering intraocular structures by damaging radiation. In addition to the advantage of an increased ablation rate as compared to laser radiation at 308 nm, this affords the significant advantage that the thermal zones of necrosis about the actual region to be removed can be reduced by the factor of 20 to 50. In this way, an optimal precision of incision is obtained with intraocular structures being shielded from the damaging wavelengths of the secondary radiation which occur during photoablation of the cornea by means of laser radiation at 193 nm.

Additional investigations have shown that the method according to the invention is advantageous also for the normal photocoagulation at the ocular fundus. For this purpose, it is preferable to use the visible laser radiation. By means of the dyes invasively applied in advance of the coagulation process, a significant increase in effectiveness is obtained and especially then when the problem is directed to the coagulation of bleeding or the proliferation of blood vessels.

The invention has been explained in detail with respect to microsurgery on the eye. However, this should not be considered a limitation with respect to the application of the method and apparatus of the invention. This application is generally applicable to surgery on biological tissues for which in addition to the UV-emitting excimer laser, also other lasers are used which emit in other wavelength ranges.

It is understood that the foregoing description is that of the preferred embodiments of the invention and that various changes and modifications may be made thereto without departing from the spirit and scope of the invention as defined in the appended claims.

What is claimed is:

1. An apparatus for performing surgery on biological pathological tissue in a region of nonpathological tissue with the aid of a laser beam applied to the pathological tissue, the apparatus comprising:

laser means for generating the laser beam with a predetermined wavelength;

transmission means for transmitting the laser beam to the site of the operation to produce a laser focus wherein the energy density in said focus is above a level to cause photoablation whereby secondary radiation is produced capable of causing damage to the nonpathological tissue;

said secondary radiation being radiation of the laser beam backscattered from the eye or fluorescence radiation of the tissue;

suction/irrigation means for removing the tissue ablated by the laser beam;

metering unit means for metering an organic-tissue penetrating substance to said site for absorbing said secondary radiation and to provide a reduced effective threshold for removing by photoablation the pathological tissue;

said substance being absorbent in the range of the wavelength of the laser beam and which increases photoablation while at the same time protecting the nonpathological tissue not treated by said laser beam against damage by said secondary radiation; and, measuring means for measuring said secondary radiation backscattered from the tissue to detect when the backscattered radiation drops or exceeds predetermined limit values selected to reduce damage to the nonpathological tissue.

2. The apparatus of claim 1, said metering unit means being connected to said suction/irrigation means.

3. The apparatus of claim 1, said transmission means comprising a light-conducting fiber for transmitting the laser beam to the site of the operation; said fiber having an end portion for applying the laser beam to said site;

said suction/irrigation means having at least one line for bringing irrigation liquid to said site; and, said apparatus further including a handheld applicator for holding said one line and said end portion.

4. The apparatus of claim 1, wherein said laser means and said transmission means conjointly produce a focus at said site having an energy density of at least 500 mJ/cm$^2$ for pulse widths of approximately 100 ms or less.

5. The apparatus of claim 1, wherein said measuring means comprises means for shutting off said laser means immediately if the values of the measured radiation increase above or drop below predetermined limit values.

6. The apparatus of claim 5, said laser means being an excimer laser radiating in the ultraviolet range and said substance being absorbent in the ultraviolet range.

7. An apparatus for performing surgery on biological pathological tissue in a region of nonpathological tissue with the aid of a laser beam applied to the pathological tissue, the apparatus comprising:

laser means for generating the laser beam with a predetermined wavelength and being adapted to apply pulses of laser radiation intermittently to the pathological tissue;

transmission means for transmitting the laser beam to the site of the operation to produce a laser focus wherein the energy density in said focus is above a level to cause photoablation whereby secondary radiation is produced capable of causing damage to the nonpathological tissue;

said secondary radiation being radiation of the laser beam backscattered from the eye or fluorescence radiation of the tissue;

suction/irrigation means for removing the tissue ablated by the laser beam;

metering unit means for metering an organic-tissue penetrating substance to said site which is absorbent in said wavelength of said laser beam and which provides a reduced effective threshold for removing by photoablation the pathological tissue;

said substance being absorbent in the range of the wavelength of the laser beam and which increases photoablation while at the same time protecting the nonpathological tissue not treated by said laser beam against damage by said secondary radiation;

measuring means for measuring the secondary radiation backscattered from the tissue to detect when the backscattered radiation drops or exceeds predetermined limit values selected to reduce damage to the nonpathological tissue; and, an electronic control unit which causes said substance to be applied to the pathological tissue during the time intervals between said pulses.

8. A method for performing surgery on the eye having pathological and nonpathological tissues while protecting the nonpathological tissue against secondary radiation during the surgery, the method comprising the steps of:

generating a pulsed laser beam of a predetermined wavelength;

focussing the laser beam on the tissue of the eye to be treated while generating an energy density at the focus adequate for photoablation whereby a secondary radiation is generated capable of causing damage to the eye tissue; and, applying an organic-tissue penetrating substance to the pathological tissue of the eye to provide a reduced effective threshold for photoablation of the pathological tissue and also applying the substance to the surrounding nonpathological tissue of the eye; said substance being absorbent in the range of the wavelength of the laser beam and which increases photoablation while at the same time protecting the nonpathological tissue not treated by said laser beam against damage by said secondary radiation.

9. The method of claim 8, wherein the substance is applied to the tissue before the laser beam is applied thereto.

10. The method of claim 8, wherein the substance is applied to the tissue during the time that the laser beam is applied to the tissue.

11. The method of claim 8, wherein the step of applying an organic tissue penetrating substance comprises applying a substance being contained in a drug having a galenic characteristic which assures that the substance will penetrate the tissue to which the laser beam is applied.

12. The method of claim 8, the laser beam being applied to a predetermined region of the eye tissue, and the method comprising the further steps of:

irrigating said region with an irrigating liquid; and, introducing said substance into said irrigating liquid.

13. The method of claim 8, comprising the further step of:

applying the laser beam to the tissue intermittently in the form of pulses to the tissue with said substance being applied to the tissue in the time intervals between said pulses.

14. The method of claim 8, wherein said step of generating include generating a pulsed laser beam radiates in the ultraviolet spectral range.

15. The method of claim 8, wherein said step of focussing while generating an energy density includes generating an energy density of at least 500 mJ/cm$^2$ at said focus for pulse widths of approximately 100 ms or less.

16. The method of claim 8, wherein said secondary radiation is scattered radiation at said wavelength.

17. The method of claim 8, wherein said secondary radiation is fluorescence radiation.

18. A method for performing surgery on the eye having pathological and nonpathological tissues while protecting the nonpathological tissue against secondary radiation during the surgery, the method comprising the steps of:
   generating a pulsed laser beam of a predetermined wavelength;
   focussing the laser beam on the tissue of the eye to be treated while generating an energy density at the focus adequate for photoablation whereby a secondary radiation is generated capable of causing damage to the eye tissue;
   applying an organic-tissue penetrating substance to the pathological tissue of the eye to provide a reduced effective threshold for photoablation of the pathological tissue and also applying the substance to the surrounding nonpathological tissue of the eye;
   said substance being absorbent in the range of the wavelength of the laser beam and which increases photoablation while at the same time protecting the nonpathological tissue not treated by said laser beam against damage by said secondary radiation; and,
   said laser beam being generated by a laser having a wavelength in the ultraviolet spectral range and said substance being a drug absorbent in said spectral range.

19. The method of claim 18, wherein the step of applying an organic tissue penetrating substance comprises applying a drug having a chemical configuration and contains aromatic ring system sin said chemical configuration which effect an ultraviolet absorption.

20. The method of claim 18, wherein said step of applying comprises applying at least one drug selected from the group consisting of:
   sulfonamides, tetracyclines, local anesthetics, beta blockers and vitamins.

21. A method for performing surgery on the eye having pathological and nonpathological tissues while protecting the nonpathological tissue against secondary radiation during the surgery, the method comprising the steps of:
   generating a pulsed laser beam of a predetermined wavelength;
   focussing the laser beam on the pathological tissue of the eye to be treated while generating an energy density at the focus adequate for photoablation whereby a backscattered secondary radiation is generated capable of causing damage to the nonpathological tissue of the eye; and,
   applying an organic-tissue penetrating substance to the pathological tissue of the eye to provide a reduced effective threshold for photoablation of the pathological tissue and also applying the substance to the surrounding nonpathological tissue of the eye; said substance being absorbent in the range of the wavelength of the laser beam and which increases photoablation while at the same time protecting the nonpathological tissue not treated by said laser beam against damage by said secondary radiation;
   measuring the secondary radiation backscattered from the eye to detect when the backscattered radiation drops or exceeds predetermined limit values selected to reduce damage to the nonpathological tissue;
   switching the laser beam off when the backscattered radiation drops or exceeds the predetermined limit values;
   applying the organic-tissue penetrating substance anew to the pathological and nonpathological tissues; and,
   switching on the laser beam to again focus the beam on the pathological tissue of the eye to be treated.

* * * * *

UNITED STATES PATENT AND TRADEMARK OFFICE
CERTIFICATE OF CORRECTION

PATENT NO. : 5,123,902

DATED : June 23, 1992

INVENTOR(S) : Gerhard Müller and Norbert Müller-Stolzenburg

It is certified that error appears in the above-identified patent and that said Letters Patent is hereby corrected as shown below:

In the title page, under "Other Publications", line 2: delete "Atheroscleratis" and substitute -- Atherosclerotic -- therefor.

In the title page, under "Other Publications", line 3: delete "Murphy Chutonan" and substitute -- Murphy Chutorian -- therefor.

In column 2, line 46: delete "opeation" and substitute -- operation -- therefor.

In column 9, line 26: delete "mirror" and substitute -- mirrors -- therefor.

In column 15, line 4: delete "include" and substitute -- includes -- therefor.

UNITED STATES PATENT AND TRADEMARK OFFICE
CERTIFICATE OF CORRECTION

PATENT NO. : 5,123,902
DATED : June 23, 1992
INVENTOR(S) : Gerhard Müller and Norbert Müller-Stolzenburg It is certified that error appears in the above-identified patent and that said Letters Patent is hereby corrected as shown below:

In column 16, line 1: delete "contains" and substitute -- containing -- therefor.

In column 16, line 1: delete "system sin" and substitute -- systems in -- therefor.

Signed and Sealed this

Twenty-eighth Day of December, 1993

Attest:

BRUCE LEHMAN

Attesting Officer            Commissioner of Patents and Trademarks